(12) United States Patent　　(10) Patent No.: US 10,653,842 B2
Haitsuka et al.　　　　　　　　　(45) Date of Patent: May 19, 2020

(54) NEEDLELESS SYRINGE

(71) Applicant: DAICEL CORPORATION, Osaka (JP)

(72) Inventors: Masahiro Haitsuka, Hyogo (JP); Toshiki Yagi, Hyogo (JP)

(73) Assignee: Daicel Corporation, Osaka (JP)

( * ) Notice: Subject to any disclaimer, the term of this patent is extended or adjusted under 35 U.S.C. 154(b) by 86 days.

(21) Appl. No.: 15/932,369

(22) Filed: Feb. 16, 2018

(65) Prior Publication Data

US 2018/0185586 A1　　Jul. 5, 2018

Related U.S. Application Data

(63) Continuation of application No. PCT/JP2015/073068, filed on Aug. 18, 2015.

(51) Int. Cl.
*A61M 5/30*　　(2006.01)
*A61M 5/315*　　(2006.01)
*A61M 5/20*　　(2006.01)

(52) U.S. Cl.
CPC ............ *A61M 5/30* (2013.01); *A61M 5/3007* (2013.01); *A61M 5/315* (2013.01); *A61M 2005/2013* (2013.01)

(58) Field of Classification Search
CPC ............ A61M 2005/2013; A61M 5/30; A61M 5/3007; A61M 5/315
See application file for complete search history.

(56) References Cited

U.S. PATENT DOCUMENTS

| 3,335,722 | A  | 8/1967 | Lowry et al. |
| 5,891,086 | A  | 4/1999 | Weston |
| 6,171,276 | B1 | 1/2001 | Lippe et al. |
| 6,425,879 | B1 | 7/2002 | Egger et al. |

(Continued)

FOREIGN PATENT DOCUMENTS

| JP | H11-514242 A | 12/1999 |
| JP | 2001-502935 A | 3/2001 |

(Continued)

OTHER PUBLICATIONS

Extended European Search Report dated Mar. 27, 2019 in corresponding European Application No. 15901685.6.

(Continued)

*Primary Examiner* — Imani N Hayman
(74) *Attorney, Agent, or Firm* — Knobbe Martens Olson & Bear LLP

(57) ABSTRACT

The described technology relates to a needleless syringe for injecting an injection objective substance into an injection target area. The needleless syringe includes a protruding member which is provided movably from a first position to a second position at which 1) a protruding length of a forward end of the protruding member from an end surface of a housing is shorter than a protruding length of the forward end at the first position and 2) the forward end and a discharge port can be brought in contact with the injection target area. The needleless syringe also includes a maintaining mechanism which maintains the protruding member at the first position and a power source circuit which applies a voltage to a driving unit when the protruding member having been maintained at the first position is moved to the second position. Accordingly, the unintended discharge from the syringe is appropriately avoided.

16 Claims, 9 Drawing Sheets

(56) References Cited

U.S. PATENT DOCUMENTS

| | | |
|---|---|---|
| 6,547,755 B1 | 4/2003 | Lippe et al. |
| 6,610,028 B1 | 8/2003 | Alexandre et al. |
| 8,133,494 B2 | 3/2012 | zur Megede et al. |
| 2001/0039394 A1 | 11/2001 | Weston |
| 2002/0007149 A1 | 1/2002 | Nelson et al. |
| 2002/0169412 A1 | 11/2002 | Haar et al. |
| 2004/0049151 A1 | 3/2004 | Lell |
| 2004/0254526 A1 | 12/2004 | Weston |
| 2004/0260234 A1 | 12/2004 | Srinivasan et al. |
| 2005/0131342 A1 | 6/2005 | Haar et al. |
| 2006/0281175 A1 | 12/2006 | McSwiggen et al. |
| 2007/0021716 A1 | 1/2007 | Hansen |
| 2007/0167907 A1 | 7/2007 | Deslierres et al. |
| 2008/0132450 A1 | 6/2008 | Lee et al. |
| 2010/0040619 A1 | 2/2010 | Li et al. |
| 2014/0296777 A1 | 10/2014 | Haitsuka et al. |
| 2017/0007768 A1 | 1/2017 | Haitsuka et al. |

FOREIGN PATENT DOCUMENTS

| | | |
|---|---|---|
| JP | 2001-513371 A | 9/2001 |
| JP | 2002-291887 A | 10/2002 |
| JP | 2003-529417 A | 10/2003 |
| JP | 2004-500933 A | 1/2004 |
| JP | 2005-523679 A | 8/2005 |
| JP | 2006-524120 A | 10/2006 |
| JP | 2007-514489 A | 6/2007 |
| JP | 2007-518460 A | 7/2007 |
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2012-065920 A | 4/2012 |
| JP | 2012-161430 A | 8/2012 |
| JP | 2015-150401 A | 8/2015 |
| WO | WO 2014/063123 A1 | 4/2014 |

OTHER PUBLICATIONS

Office Action dated Jul. 4, 2017 in related Japanese Application No. 2014-029865.
International Search Report dated Oct. 27, 2015 in International Application No. PCT/JP2015/073068.
International Preliminary Report on Patentability dated Feb. 20, 2018 in related International Application No. PCT/JP2015/073068.
Office Action dated Feb. 27, 2018 in related Japanese Application No. 2014-029865.

NEEDLELESS SYRINGE

CROSS-REFERENCE TO RELATED APPLICATIONS

This application is a continuation application, and claims the benefit under 35 U.S.C. §§ 120 and 365 of PCT Application No. PCT/JP2015/073068, filed on Aug. 18, 2015, which is hereby incorporated by reference.

TECHNICAL FIELD

The present disclosure relates to a needleless syringe with which an injection objective substance is injected into an injection target area without using any injection needle.

BACKGROUND ART

A syringe is known, with which an injection component is discharged or injected by utilizing the energy of a combustion gas produced by the ignition of a propellant or explosive. For example, in the case of a syringe described in Patent Literature 1, a current flows through a filament by supplying an ignition current from a battery to an ignition device, and an injection solution is discharged in accordance with the combustion of the propellant. The current supply from the battery is executed by a user by intruding or depressing a diaphragm provided at an end portion of the syringe.

SUMMARY

Problems to be Solved

According to the conventional technique, the needleless syringe, which discharges the injection component without using any injection needle by utilizing, for example, the combustion energy of the propellant, is constructed such that the propellant is ignited by using the starting point of the pressing action performed by the user. On this account, if the combustion of the propellant is performed on account of any erroneous operation of the user, there is a possibility that the injection solution may be discharged in an unintended state. In general, in the case of the needleless syringe, it is necessary that the injection solution should penetrate through the surface of the injection target area (for example, human skin or the like). Therefore, the injection solution, which is suitably pressurized by the combustion of the propellant, is discharged. Therefore, it is necessary to avoid the unintended discharge of the injection solution.

In the preceding technical document described above, a safety member, which covers the diaphragm that is the operation portion for the user, when the syringe is not used, is arranged so that any unintended discharge of the injection solution is not performed. However, the discharge port, from which the injection solution is discharged, is not necessarily in such a state that the discharge port is brought in contact with the injection target area, during the use as well. Therefore, the following possibility remains to no small extent. That is, for example, when the user removes the safety member in order to use the syringe, then the diaphragm may be unintentionally depressed, and the injection solution may be erroneously discharged.

Further, in the case of such a syringe that an injection solution is delivered to an injection target area by discharging the injection solution without using any injection needle by using, as a driving source, the energy other than the combustion energy of the propellant, the injection solution is also pressurized in many cases by using the operation of the user as the starting point. On this account, even in the case of the situation as described above, any unintended discharge of the injection solution may be caused, for example, by any erroneous operation performed by the user as described above.

In view of the above, taking the foregoing problems into consideration, an object of the present disclosure is to appropriately avoid the unintended discharge from a syringe which discharges an injection objective substance such as an injection solution or the like without using any injection needle.

Means for Solving the Problems

In order to solve the problems as described above, the present disclosure resides in a syringe for discharging an injection objective substance (for example, an injection solution) without using any injection needle, wherein the voltage application, which is performed with respect to a driving unit, is correlated with an injection operation performed by a user, i.e., the operation, in which a discharge port of the syringe is brought in contact with an injection target area in order to perform the injection by the user, is mechanically correlated with the voltage application which performed with respect to the driving unit. Accordingly, the execution of a series of operations performed by the user in order to carry out the injection is an requirement to permit the discharge of the injection objective substance. Therefore, it is possible for the user to precisely avoid any unintended discharge of the injection objective substance.

Specifically, the present disclosure resides in a needleless syringe for injecting an injection objective substance into an injection target area by discharging the injection objective substance without using any injection needle; the needleless syringe comprising an accommodating unit which is provided in a housing of the needleless syringe and which accommodates the injection objective substance; a driving unit which is operated when a voltage is applied to generate discharge energy in order to discharge the injection objective substance accommodated in the accommodating unit; a nozzle unit which includes a flow passage for allowing the injection objective substance applied with the discharge energy generated by the driving unit to flow therethrough and which discharges the injection objective substance from a discharge port formed at a forward end of the flow passage; a protruding member which is provided movably from a first position at which a forward end thereof protrudes from an end surface of the housing to a second position at which a protruding length of the forward end from the end surface of the housing is shorter than a protruding length provided at the first position and the forward end and the discharge port can be brought in contact with the injection target area; a maintaining mechanism which maintains the protruding member at the first position before the discharge energy is generated by the driving unit; and a power source circuit which applies a voltage to the driving unit when the protruding member having been maintained at the first position is moved to the second position by means of a pressing force received by the forward end of the protruding member.

In the needleless syringe according to the present disclosure, as for the driving unit, it is possible to adopt, as the energy source, a variety of known energy generating forms, provided that the energy is generated in order to discharge the injection objective substance by means of the voltage application from the power source circuit, and the energy can be transmitted to the injection objective substance. For example, it is possible to adopt an ignition charge which is ignited by an ignition device and a gas generating agent which produces the gas by means of the combustion. Further, as for other forms of the driving unit other than the above, it is also allowable to adopt such a structure that the release of the energy of an elastic member such as a spring or the like or the energy of the compressed gas is controlled by the voltage application from the power source circuit. For example, an electromagnetic valve, a solenoid actuator or the like, which is driven by the voltage application from the power source circuit, is utilized to release a piston fixed by an urging spring from a fastened state, and thus the accumulated elastic energy of the urging spring can be utilized as the discharge energy.

Note that when the combustion energy of the propellant is utilized as the discharge or ejection energy, the ignition charge may be, for example, any one of propellants including a propellant containing zirconium and potassium perchlorate, a propellant containing titanium hydride and potassium perchlorate, a propellant containing titanium and potassium perchlorate, a propellant containing aluminum and potassium perchlorate, a propellant containing aluminum and bismuth oxide, a propellant containing aluminum and molybdenum oxide, a propellant containing aluminum and copper oxide, and a propellant containing aluminum and ferric oxide, or a propellant composed of a combination of a plurality of propellants described above. The feature of the ignition charge as described above is as follows. That is, the combustion product thereof does not contain any gas component at the ordinary temperature even if the combustion product is a gas in a high temperature state. Therefore, the combustion product is immediately condensed after the ignition. As a result, when the syringe of the present disclosure is used for the injection into the living body, it is possible to efficiently perform the injection into a shallower portion of the injection target area of the living body. Further, when the energy generated by a gas generating agent is utilized as the discharge or ejection energy, it is also possible to use, as the gas generating agent, a single base smokeless propellant and various gas generating agents used for a gas generator for the air bag and a gas generator for the seat belt pretensioner.

The discharge energy, which is brought about by the driving unit, is transmitted to the injection objective substance accommodated in the accommodating unit. The injection objective substance is extruded along the flow passage formed in the nozzle unit, and the injection objective substance is finally discharged from the discharge port toward the injection target area. In relation thereto, in the case of the conventional technique, the operation, which is executed in order to apply the voltage from the power source circuit to the driving unit, is performed independently from the preparatory operation for the injection with the needleless syringe, i.e., the operation which is performed in order that the discharge port, which is provided for the nozzle unit, is confronted with the injection target area, the discharge port being brought in contact with the surface of the injection target area in order to efficiently deliver the injection objective substance into the injection target area in many cases in accordance with the operation (hereinafter simply referred to as "preparatory operation"). That is, in the case of the conventional technique, the preparatory operation is performed, and the operation performed by a user in order to execute the discharge (for example, the operation is exemplified by the depression or the like of an operation button for executing the voltage application in order to perform the discharge, and the operation is referred to as "discharge execution operation") is executed in a state in which the preparatory operation is completed. However, when the preparatory operation and the discharge execution operation are independent from each other, it is impossible to sweep away such a possibility that the discharge execution operation may be erroneously performed and the discharge of the injection objective substance not intended by the user may be performed in a state in which the preparatory operation is not completed, i.e., a state in which the positioning of the discharge port is not completed with respect to the injection target area.

In view of the above, in the case of the needleless syringe according to the present disclosure, the protruding member is provided, which has the forward end that protrudes from the end surface of the housing. The protruding member is the member which protrudes in the discharge direction from the discharge port for the injection objective substance. The protruding member is constructed so that the protruding member is movable between the first position and the second position in relation to the protruding state thereof. The first position is the position at which the protruding member is located by the maintaining mechanism before the needleless syringe is used, i.e., before the discharge energy is generated by the driving unit. The first position is the position at which the forward end portion of the protruding member at least protrudes in the discharge direction as compared with the position of the discharge port of the needleless syringe. Therefore, if the user intends to inject the injection objective substance into the injection target area, the protruding member, which is disposed at the first position, is brought in contact with the surface of the injection target area prior to the discharge port.

Then, the second position is the position at which the protruding member is located when the protruding member is intruded into the inside of the housing by means of the external force. Therefore, the protruding length of the forward end portion from the end surface of the housing provided at the second position is shorter than the protruding length provided at the first position. Note that the protruding length according to the present disclosure resides in the concept which indicates the amount of protrusion of the protruding member from the end surface of the housing, which also includes such a state that the protruding member is flush with the end surface, i.e., such a state that the amount of protrusion is zero. Then, the needleless syringe is constructed as follows. That is, when the protruding member arrives at the second position by means of the pressing force received by the forward end thereof from the injection target area, then such a state is formed that the forward end of the protruding member and the discharge port are brought in contact with the injection target area, and the voltage application from the power source circuit to the driving unit is executed. This fact means that the discharge execution operation is executed cooperatively at the point in time at which the preparatory operation performed by the user is completed, i.e., the point in time at which such a state that the discharge port and the injection target area are brought in contact with each other is formed. Therefore, in the case of the needleless syringe according to the present disclosure, the preparatory operation and the discharge execution operation are not the operations which are independent from each other respectively, and the preparatory operation and the discharge execution operation are mechanically correlated with each other by the aid of the protruding member. Accordingly, it is possible to avoid such a situation that the user erroneously executes the discharge execution operation in a state in which the preparatory operation is not completed.

In other words, the needleless syringe according to the present disclosure is constructed such that the discharge execution operation is not permitted if the user does not perform the preparatory operation with a definite intention. Therefore, in order to perform the discharge execution operation, for example, such an operation is required that the user intentionally applies the load to the syringe to press the syringe against the injection target area. Therefore, it is necessary that the load, which is required for the protruding member to move from the first position to the second position, should be also adjusted depending thereon, and the adjustment may be performed, for example, by means of the maintaining mechanism. Note that it is possible to adopt a variety of mechanisms for the protruding member, provided that the protruding member can be moved in the direction opposite to the direction in which the needleless syringe is pressed against the injection target area, when the needleless syringe is pressed against the injection target area.

Further, in the case of the needleless syringe according to the present disclosure, the forward end of the nozzle unit may be flush with the end surface of the housing. Alternatively, the nozzle unit may be in such a state that the nozzle unit protrudes from the end surface of the housing. In the case of the former, the second position, at which the protruding member is located, is the position at which the protruding length is zero. In the case of the latter, the second position, at which the protruding member is located, is the position at which the protruding length is the same as the amount of protrusion of the nozzle unit from the end surface of the housing (protruding length is not zero) in some cases, or the protruding length is smaller than the amount of protrusion of the nozzle unit in other cases.

Note that, as for the syringe according to the present disclosure, the injection objective substance includes the component which is expected to exhibit the efficacy at the objective portion of the injection target area. Therefore, an accommodation state of the injection objective substance in the accommodating unit and a specific physical form of the injection objective substance such fluid in a liquid or gel form, powder, granular solid is not particularly limited as long as that the discharge can be performed at least by the energy applied by the driving unit. For example, the injection objective substance may be a liquid. Alternatively, the injection objective substance may be a solid in a gel form provided that the fluidity, which enables the discharge, is secured, even when the injection objective substance is the solid. The injection objective substance may contain a component which is to be delivered to the objective portion. The component may exist in a state of being dissolved in the injection objective substance or may exist in a simply mixed state without being dissolved. Examples of the component to be delivered include vaccines for enhancing antibody, proteins for cosmetic treatments, and cultured cells for regenerating hair. These components are contained in fluid in a liquid or gel form so that the components can be injected, whereby the injection objective substance is formed.

In this context, in the needleless syringe described above, the protruding member may be formed by an annular member which surrounds the discharge port. If the needleless syringe is constructed such that the protruding member surrounds the discharge port as described above, when the injection objective substance is discharged, then a part of the injection objective substance, which does not enter the inside of the injection target area, can be thereby shut off by means of the annular protruding member, and it is possible to avoid the scattering around the user. Further, even when the protruding member is not annular, if the protruding member is formed to surround the discharge port in a state in which a part of the protruding member is cut out, then it is also possible to more reliably avoid the scattering of the injection objective substance by shortening the cutout distance.

Further, the needleless syringe may comprise a plurality of the protruding members. In this case, the voltage application from the power source circuit to the driving unit is executed in accordance with movement of all of the plurality of protruding members to the second position. When the needleless syringe is constructed as described above, the movement of all of the protruding members to the second position serves as the trigger for the voltage application. Therefore, it is possible to prompt the user to perform the more careful preparatory operation. It is possible to more precisely avoid the unintended discharge of the injection objective substance. Further, from another viewpoint, the structure as described above makes it possible for the user to control the attitude or posture of the needleless syringe with respect to the injection target area in order to move all of the protruding members to the second position in order that the injection is performed. The structure contributes to realize the appropriate injection.

Further, when the plurality of protruding members are provided as described above, the plurality of protruding members may be arranged in a circumferential direction around the discharge port on the end surface of the housing. In this case, it is preferable that the respective protruding members are arranged so that distances from the nozzle unit are identical with each other. Owing to the structure as described above, the attitude or posture of the needleless syringe with respect to the injection target area can be a more appropriate attitude or posture about the center of the discharge port (for example, an attitude or posture orthogonal to the injection target area).

Further, when the plurality of protruding members are provided as described above, then the housing may have a visual recognition window which is provided on a side surface thereof in order to visually recognize an interior; and the accommodating unit may be formed so that the accommodated injection objective substance can be visually recognized from outside through the visual recognition window. In this case, it is preferable that the plurality of protruding members are arranged respectively so that the plurality of protruding members are not overlapped with the visual recognition window before and after the movement from the first position to the second position. Owing to the structure as described above, the visual recognition of the injection objective substance, which is performed by the user through the visual recognition window, can be reliably secured without disturbing the effect brought about by the plurality of protruding members (precise prevention of any unintended discharge of the injection objective substance and attitude or posture maintenance of the needleless syringe).

In this context, the needleless syringe described above may further comprise a syringe unit which collectively stores, as one unit, the accommodating unit, the driving unit, and the nozzle unit in the housing, so that the discharge port of the nozzle unit is arranged at a forward end of the unit. In this case, it is preferable that the protruding member is formed as the syringe unit, and the first position is a position at which the forward end of the syringe unit protrudes from the end surface of the housing. Owing to the structure as described above, it is possible to allow the syringe unit itself to function as the protruding member according to the present disclosure. Specifically, the syringe unit, which is located at the first position, is intruded into the housing to move to the second position in a state in which the discharge port and the injection target area are brought in contact with each other. Accordingly, the voltage application from the power source circuit to the driving unit is executed. As a result, the preparatory operation and the discharge execution operation of the user can be mechanically correlated with each other. Thus, it is possible to avoid any unintended discharge of the injection objective substance.

Further, the needleless syringe described above may further comprise an annular elastic cover which is arranged on the end surface of the housing and which surrounds the forward end of the syringe unit. In this case, it is preferable that the cover is formed so that a protruding length of the forward end of the cover from the end surface of the housing is not less than a protruding length of the forward end of the syringe unit from the end surface of the housing when the syringe unit is disposed at the first position, and the cover allows the syringe unit to move to the second position by being elastically deformed by the pressing force when the syringe unit is intruded by the pressing force. If the forward end of the cover is flush with the forward end of the syringe unit or the forward end of the cover protrudes therefrom when the syringe unit is disposed at the first position, it is thereby possible to avoid any careless action of the pressing force exerted on the syringe unit. Then, the elastic member is progressively deformed by the pressing force, and thus the syringe unit can be moved from the first position to the second position. On this account, in order to apply the voltage to the driving unit, it is necessary to move against the elastic force of the elastic member. Therefore, even if any pressing force carelessly acts on the syringe unit, it is possible to avoid any useless occurrence of the voltage application.

In this context, the needleless syringe described above may further comprise an operation switch which is operated in accordance with an operation of a user in relation to the voltage application from the power source circuit to the driving unit in a direction different from a direction of the movement of the protruding member from the first position to the second position. In this case, the voltage application from the power source circuit to the driving unit is executed when the protruding member arrives at the second position and the operation switch is operated so that the voltage can be applied. That is, the needleless syringe resides in the disclosure which correlates the operation of the operation switch as the injection execution operation with the preparatory operation, in addition to the operation to move the protruding member from the first position to the second position. In relation thereto, the setting is made such that the former operation direction is different from the latter operation direction. Thus, the both operations in the injection execution operation can be made independent from each other. Accordingly, in order to apply the voltage to the driving unit, the requirement of the execution of the operation of the operation switch is imposed on the user distinctly from the operation to bring the discharge port in contact with the injection target area in order to apply the voltage to the driving unit. Therefore, it is possible to more precisely avoid any unintended discharge of the injection objective substance.

In this context, the following form can be exemplified as the form of the maintaining mechanism for maintaining the protruding member at the first position. For example, as for the needleless syringe described above, the maintaining mechanism may have an urging member which urges the protruding member in a protruding direction thereof by means of a predetermined urging force. In the case of the structure as described above, the protruding member is progressively intruded against the predetermined urging force brought about by the urging member. Accordingly, the protruding member can be moved to the second position, and it is possible to execute the voltage application to the driving unit. Note that the predetermined urging force determines the easiness of the movement of the protruding member to the second position. Therefore, the predetermined urging force may be determined while considering, for example, the convenience of the user and the effectiveness of the prevention of the unintended discharge of the injection objective substance.

Further, as another form of the maintaining mechanism, as for the needleless syringe described above, the maintaining mechanism may be formed in such a fitting relationship that the maintaining mechanism maintains the protruding member at the first position against the pressing force if the pressing force is not more than a predetermined value, while the maintaining mechanism allows the protruding member to move to the second position if the pressing force is larger than the predetermined value. In the case of the structure as described above, the fitting relationship is released when the pressing force exerted on the protruding member exceeds the predetermined value. The protruding member can be moved to the second position, and it is possible to execute the voltage application to the driving unit. Note that the magnitude of the predetermined value determines the easiness of the movement of the protruding member to the second position. Therefore, the magnitude of the predetermined value may be determined while considering, for example, the convenience of the user and the effectiveness of the prevention of the unintended discharge of the injection objective substance in the same manner as the form described above.

It is possible to appropriately avoid the unintended discharge from the syringe which discharges the injection objective substance such as the injection solution or the like without using any injection needle.

DETAILED DESCRIPTION OF EMBODIMENTS

An explanation will be made below with reference to the drawings about a needleless syringe 1 according to an embodiment of the present disclosure (hereinafter simply referred to as "syringe 1"). Note that the structure of the following embodiment is described by way of example, and the present disclosure is not limited to the structure of the embodiment.

First Embodiment

<Structure of Syringe 1>

Figure 1:
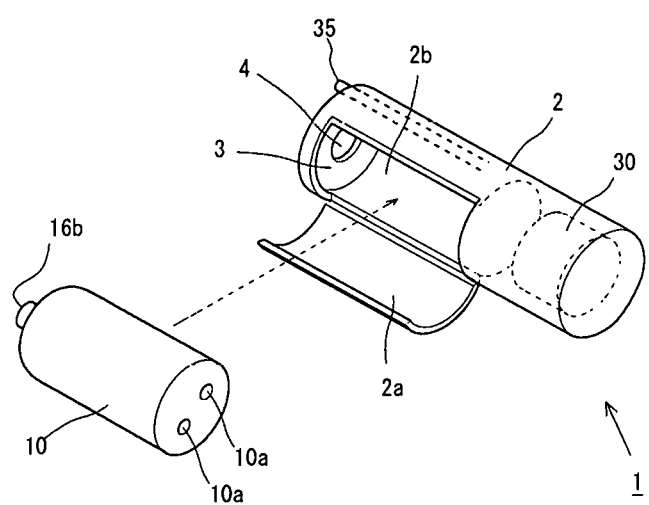
FIG. 1 shows a first drawing illustrating a schematic structure of a needleless syringe according to the present disclosure.
Figure 2:
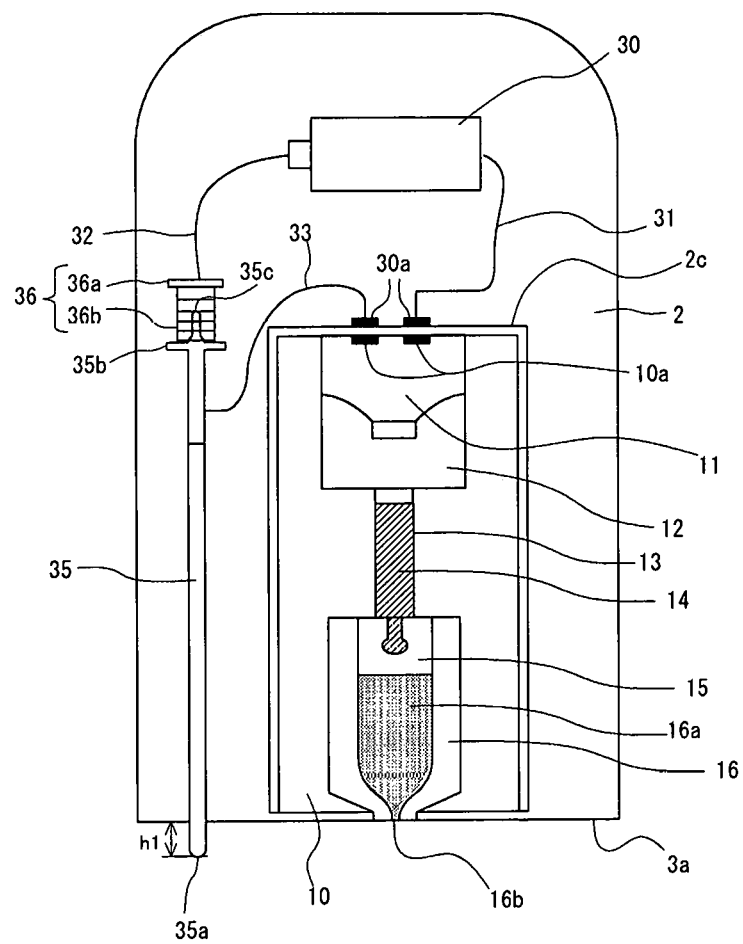
FIG. 2 shows a second drawing illustrating a schematic structure of the needleless syringe according to the present disclosure.

In this specification, FIGS. 1 and 2 shows a schematic structure of the syringe 1. FIG. 1 shows a perspective view illustrating the syringe 1, and FIG. 2 shows a sectional view of the syringe 1 taken in a longitudinal direction thereof. The syringe 1 is formed by charging a syringe unit 10 described later on into a housing 2. Note that, in the following description of this specification, the injection objective substance, which is injected into an injection target area by the syringe 1, is generally referred to as "injection solution". However, this does not intend to limit the content and the form of the substance to be injected. As for the injection objective substance, it is allowable that the component, which is to be delivered, for example, to the skin structure as the injection target area, is either dissolved or undissolved. Further, no problem arises in relation to the specified form of the injection objective substance as well, provided that the injection objective substance can be discharged with respect to the injection target area from a nozzle 16a by being pressurized. It is possible to adopt various forms including, for example, liquid and gel forms.

The syringe 1 is constructed so that the syringe unit 10 is detachable with respect to the housing 2. The syringe unit 10 is the unit which is used once and then thrown away every time when the injection solution is discharged. On the other hand, the housing 2 includes a battery 30 which supplies the electric power to an igniter 11 included in the syringe unit 10. The housing 2 is the unit which can be repeatedly used as long as the electric power capable of being supplied to the igniter 11 remains in the battery 30. Note that the battery 30 may be exchangeable as well.

In this arrangement, the syringe unit 10 has a body which is formed to be cylindrical. The syringe unit 10 has therein the igniter 11 which is an electric igniter for generating the energy for the discharge by combusting a propellant or explosive component. The syringe unit 10 is in a state of being incorporated with a piston 14 which transmits the energy brought about by the igniter 11 to the side of an accommodating unit 16 as described later on. In particular, the syringe unit 10 has the body which is produced by means of the injection molding of a resin. A known method can be used for the injection molding. In this case, the igniter 11 is positioned in the body so that the piston 14 is positioned in a direction of the release of the combustion gas produced by the combustion of an ignition charge in the igniter 11. The insert molding is performed so that the igniter 11 and the body are integrated into one unit: Note that as for the resin material for the body of the syringe unit 10, it is possible to use, for example, known nylon 6-12, polyarylate, polybutylene terephthalate, polyphenylene sulfide, or liquid crystal polymer. A filler or packing material such as glass fiber, glass filler or the like may be contained in the resin as described above. 20 to 80% by mass of glass fiber can be contained in polybutylene terephthalate, 20 to 80% by mass of glass fiber can be contained in polyphenylene sulfide, and 20 to 80% by mass of mineral can be contained in liquid crystal polymer. Further, a metal may be used in combination for a part for which the heat resistance and/or the pressure resistance is/are required.

In this case, the ignition charge used in the igniter 11 is preferably exemplified by a propellant containing zirconium and potassium perchlorate (ZPP), a propellant containing titanium hydride and potassium perchlorate (THPP), a propellant containing titanium and potassium perchlorate (TiPP), a propellant containing aluminum and potassium perchlorate (APP), a propellant containing aluminum and bismuth oxide (ABO), a propellant containing aluminum and molybdenum oxide (AMO), a propellant containing aluminum and copper oxide (ACO), a propellant containing aluminum and ferric oxide (AFO), and a mixture of some of the aforementioned propellants. The propellants as described above have the following characteristics. That is, the plasma at a high temperature and a high pressure is generated during the combustion immediately after the ignition. However, when the temperature becomes the ordinary temperature, and the combustion product is condensed, then the generated pressure is suddenly lowered, because no gas component is contained. It is also allowable that any propellant other than the above is used as the ignition charge, provided that the appropriate injection can be performed.

Note that a combustion chamber 12 is formed in front of the igniter 11 (in the direction in which the combustion gas is released). A through-hole 13, which has a constant diameter in the axial direction, is provided, which is connected to the combustion chamber 12. Then, the remaining end of the through-hole 13 arrives at a space for accommodating the accommodating unit 16. The piston 14 made of metal is arranged in the through-hole 13 so that the piston 14 can be propelled in the axial direction in the through-hole 13. One end thereof is directed toward the combustion chamber 12. Further, the remaining other end is connected to a plunger 15 for enclosing the injection solution in the accommodating unit 16.

An explanation will now be made about the accommodating unit 16 enclosing the injection solution. The plunger 15 is formed of a resin material. For example, butyl rubber and silicon rubber can be adopted as the material for the plunger 15. Further, examples of the material include styrene-based elastomer, hydrogenated styrene-based elastomer, and the styrene-based elastomer and the hydrogenated styrene-based elastomer added with polyethylene, polypropylene, polybutene, polyolefin such as α-olefin copolymer, liquid paraffin, oil such as process oil, and powder inorganic matters such as talc, cast, and mica. Further, polyvinyl chloride-based elastomer, olefin-based elastomer, polyester-based elastomer, polyamide-based elastomer, and polyurethane-based elastomer, various rubber materials (in particular, those subjected to vulcanization) such as natural rubber, isoprene rubber, chloroprene rubber, nitrile-butadiene rubber, and styrene-butadiene rubber, mixtures of the kinds of elastomer and the kinds of rubber, and the like can be adopted as the material for the plunger.

The plunger 15 is arranged in the accommodating unit 16 as described above, and thus a hermetically closed space 16a for enclosing the injection solution is formed in the accommodating unit 16. Further, a nozzle 16b, which is provided to discharge the injection solution to the outside, is formed at a forward end of the accommodating unit 16, i.e., at an end portion disposed on the side opposite to an end portion at which the plunger 15 is inserted. In the syringe unit 10 constructed as described above, the interior of the combustion chamber 12 is in a state of high temperature and high pressure by means of the combustion gas produced by the combustion of the propellant in the igniter 11. As a result, the piston 14 is propelled in the through-hole 13 by means of the pressurization. The injection solution, which has been accommodated in the hermetically closed space 16a, is pressurized. The injection solution is discharged from the discharge port of the nozzle 16b to the outside.

Further, any additional powder component is not specifically arranged in the combustion chamber 12 shown in FIG. 2. However, in order to adjust the pressure transition applied to the injection solution by the aid of the piston 14, a gas generating agent or the like, which is combusted by the combustion product produced by the combustion of the propellant in the igniter 11 and which produces the gas, can be also arranged in the combustion chamber 12. An example of the gas generating agent is exemplified by a single base smokeless propellant composed of 98% by mass of nitrocellulose, 0.8% by mass of diphenylamine, and 1.2% by mass of potassium sulfate. Further, it is also possible to use a variety of gas generating agents used for a gas generator for the air bag and a gas generator for the seat belt pretensioner. It is possible to change the combustion completion time of the gas generating agent by adjusting the dimension, the size, and the shape, especially the surface shape of the gas generating agent arranged in the combustion chamber 12. Accordingly, the pressure transition to be applied to the injection solution can be a desired transition, i.e., a transition with which the injection solution can appropriately arrive at the injection target area. In the present disclosure, the igniter 11 arranged in the combustion chamber 12 is using as the driving unit. And the gas generating agent or the like, which is optionally used, is also included in the driving unit.

As shown in FIG. 1, the syringe unit 10, which is constructed as described above, is installed to an accommodating space 2b from an opening provided on the side surface of the housing 2. In this process, the nozzle 16b, which is positioned at the forward end portion of the accommodating unit 16, is fitted into a through-hole 4 which is provided on a forward end surface 3 of the housing 2. The fixation is effected in the accommodating space 2b in a state in which the proximal end side of the syringe unit 10 (end portion disposed on the side opposite to the forward end portion provided with the nozzle 16b) is pressed against a bottom surface 2c positioned at the deep portion of the accommodating space 2b by means of fixing means brought about by an unillustrated elastic member. As a result, the positioning is effected in a state in which a connecting terminal 10a for the igniter 11, which is provided on the end surface of the syringe unit 10 on the side of the proximal end portion, is brought in contact with a connecting terminal 30a on the side of the battery 30 provided on the bottom surface 2c. Note that FIG. 2 is depicted in a state in which the connecting terminals 10a, 30a are intentionally separated from each other in order to more comprehensively understand the structure of the syringe 1. In this fixation state, if the voltage is applied from the battery 30 to the igniter 11 by the aid of the connecting terminals 10a, 30a which are brought in contact with each other, the discharge of the injection solution is executed in accordance with the combustion of the propellant.

Note that the opening to arrive at the accommodating space 2b of the housing 2 is provided with a door portion 2a for opening/closing the opening. When a user installs the syringe unit 10 to the housing 2 upon the use of the syringe 1, the user can access the opening by opening the door portion 2a. When the installation of the syringe unit 10 is completed, it is possible to suppress the abrupt disengagement of the syringe unit by closing the door portion 2a.

An explanation will now be made about the structure which relates to the operation for discharging the injection solution with the syringe 1, i.e., the operation for applying the voltage from the battery 30 to the igniter 11. In the syringe 1, the execution of the voltage application from the battery 30 to the igniter 11 is controlled by the switch constructed by switch members 35, 36. That is, a circuit for applying the voltage from the battery 30 to the igniter 11 is formed by the switch members 35, 36. In this case, the switch member 35 is formed to have a stick-shaped form. The switch member 35 is arranged in the housing 2 in the longitudinal direction of the housing 2 so that the switch member 35 is slidable in the longitudinal direction. In the state shown in FIG. 2, a forward end portion 35a of the switch member 35 protrudes from an end surface 3a of the forward end portion of the housing 2. The height of protrusion is represented by h1. Then, a brim portion 35b is provided in the vicinity of the proximal end of the switch member 35. Further, a proximal end portion 35c is arranged. In this arrangement, the connecting terminal 30a arranged on the bottom surface 2c is connected to the portion disposed in the vicinity of the brim portion 35b of the switch member 35 via a wiring 33 in the housing 2. Accordingly, an electric conduction state is formed between one of the connecting terminals 30a and the proximal end portion 35c. Note that the forward end portion 35a of the switch member 35 is constructed so that the insulation state is retained with respect to the proximal end portion 35c. Further, the other of the connecting terminals 30a (connecting terminal 30a not connected to the switch member 35) is connected to the minus terminal of the battery 30.

In the next place, the switch member 36 has a brim portion 36a made of metal which is fixed in the housing 2 and which is connected to the plus terminal of the battery 30, and a spring portion 36b which is composed of an insulating material. The spring portion 36b has both ends thereof which are connected to the brim portion 35b of the switch member 35 and the brim portion 36a of the switch member 36. Therefore, the spring portion 36b is elastically deformed depending on the position of the switch member 35 which is arranged slidably in the housing 2 to apply the urging force depending on the amount of elastic deformation with respect to the switch member 35. Note that the spring portion 36b is made of the insulating material. Therefore, any electric conduction state is not given between the brim portion 35b and the brim portion 36a via the spring portion 36b. Note that the switch member 35 corresponds to the protruding member which is referred to in the present disclosure. The spring portion 36b corresponds to the maintaining mechanism which maintains such a state that the forward end portion 35a of the switch member 35 protrudes from the end surface 3a of the housing 2 in the state provided before the operation.

In this arrangement, in the state in which any external force is not exerted on the switch member 35 arranged slidably, as shown in FIG. 2, the forward end portion 35a is maintained in such a state that the forward end portion 35a protrudes by the height h1 from the surface 3a of the forward end surface 3 of the housing 2, i.e., the end surface at which the discharge port of the nozzle 16b for discharging the injection solution is arranged, owing to the presence of the spring portion 36b. The position of the switch member 35, which is provided in the protruding state, corresponds to the first position according to the present disclosure. In this situation, the switch member 35 and the switch member 36 are disposed in a state in which the switch member 35 and the switch member 36 are not electrically brought in contact with each other by the aid of the spring portion 36b (hereinafter referred to as "non-contact state"). Therefore, such a state is not given that the output voltage of the battery 30 is applied to the igniter 11 via the connecting terminals 10a, 30a.

Figure 3A:
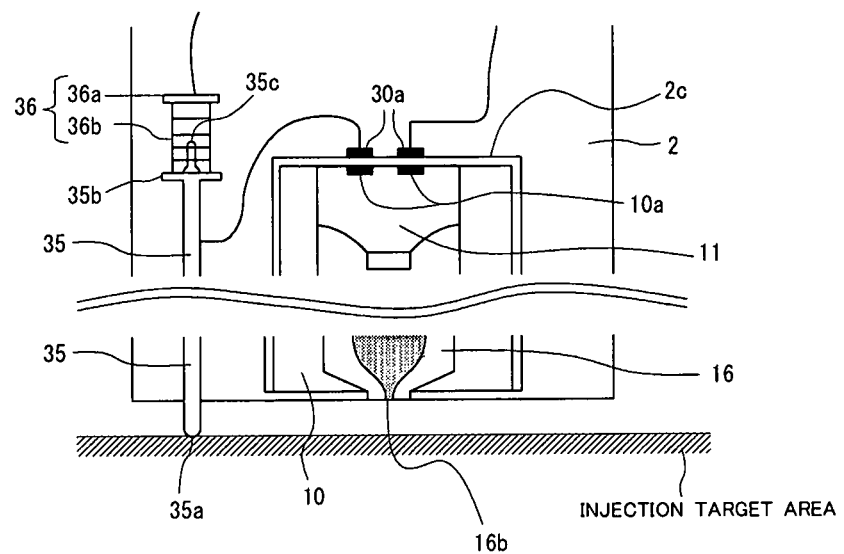
FIG. 3A shows the action of a switch mechanism of the needleless syringe according to the present disclosure.

When the user intends to inject the injection solution into the injection target area by using the syringe 1, it is necessary to perform the preparatory operation in which the discharge port of the nozzle 16b is brought in contact with the surface of the injection target area and the discharge execution operation in which the voltage is applied to the igniter 11 in order to discharge the injection solution. Accordingly, as shown in FIG. 3A, when the user intends to bring the discharge port of the nozzle 16b in contact with the surface of the injection target area as the preparatory operation, the forward end portion 35a is brought in contact with the injection target area before the discharge port is brought in contact with the injection target area, because the forward end portion 35a of the switch member 35 protrudes by the height h1 as described above. Note that even when the forward end portion 35a is merely brought in contact with the injection target area, the switch member 35 does not slide into the housing 2, on account of the urging force exerted by the spring portion 36b.

Figure 3B:
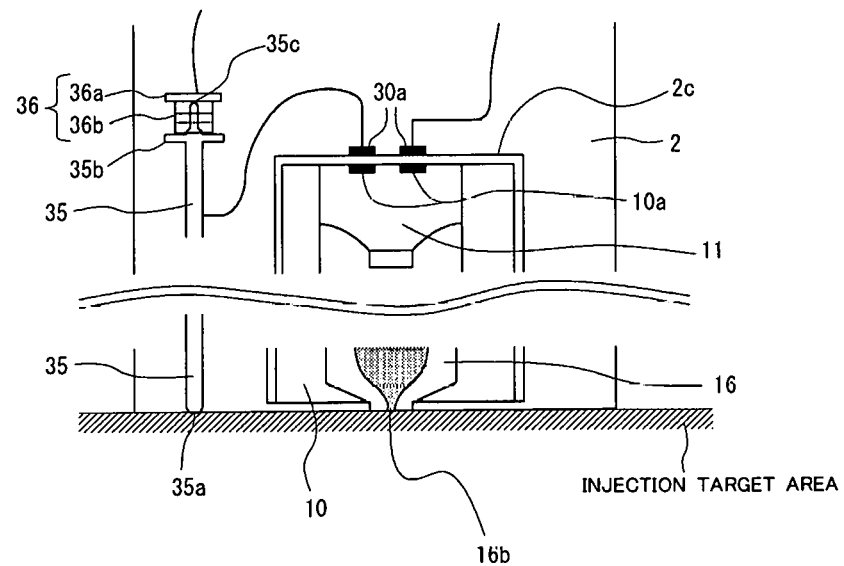
FIG. 3B shows the action of a switch mechanism of the needleless syringe according to the present disclosure.

Then, the syringe 1 is allowed to approach the injection target area by the user while maintaining the state in which the forward end portion 35a is brought in contact with the injection target area to give a state shown in FIG. 3B, i.e., a state in which the discharge port of the nozzle 16b is brought in contact with the injection target area. In this situation, the spring portion 36b is connected to the switch member 35. Therefore, the user intrudes the switch member 35 into the interior of the housing 2 against the urging force, and thus the discharge port of the nozzle 16b is brought in contact with the surface of the injection target area to complete the preparatory operation for the injection. The position of the switch member 35 intruded into the interior of the housing 2 as described above corresponds to the second position according to the present disclosure.

At the point in time at which the preparatory operation is completed, the switch member 35 slides into the housing 2 by the amount corresponding to the initial protruding height h1. Therefore, the spring portion 36b is compressed by the amount corresponding to the slide amount. Then, in the state in which the spring portion 36b is compressed, the proximal end portion 35c of the switch member 35 is brought in contact with the brim portion 36a of the switch member 36. Therefore, the switch member 35 and the switch member 36 are in the electric conduction state. The output voltage of the battery 30 is applied to the connecting terminal 30a. The voltage is applied via the connecting terminal 10a to the igniter 11 arranged in the syringe unit 10, and the injection solution is discharged.

In the case of the syringe 1 in which the voltage application to the igniter 11 is controlled by using the starting point of the slide of the switch member 35 into the interior of the housing 2 as described above, when the user starts the preparatory operation in which the discharge port of the nozzle 16b is brought in contact with the injection target area, and the preparatory operation is completed, then the voltage application to the igniter 11 is cooperatively executed in accordance with the contact between the switch members 35, 36 corresponding to the discharge execution operation. That is, in the case of the syringe 1, the preparatory operation and the discharge execution operation are mechanically correlated with each other by the aid of the switch member 35 which especially performs the slide movement. Accordingly, it is possible to avoid such a situation that the user erroneously executes the discharge execution operation in a state in which the preparatory operation is not completed. In other words, the voltage application to the igniter 11 is not executed if the state, in which the discharge port of the nozzle 16b is brought in contact with the injection target area, is not given. Therefore, in the case of the syringe 1, it is possible to avoid the unintended discharge of the injection solution.

First Modified Embodiment

Figure 4A:
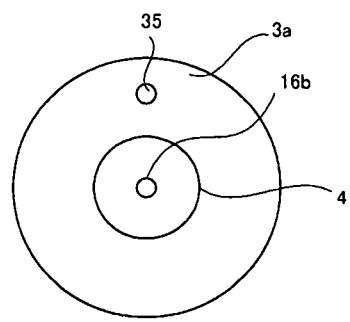
FIG. 4A shows front views illustrating needleless syringes according to the present disclosure.
Figure 4B:
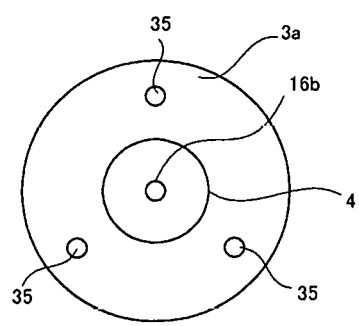
FIG. 4B shows front views illustrating needleless syringes according to the present disclosure.

A first modified embodiment of the syringe 1 will now be explained on the basis of FIGS. 4A and 4B. FIG. 4A shows front views illustrating syringes 1 as viewed from the forward end side. In the embodiment described above, as shown in FIG. 4A, one switch member 35 is arranged, which protrudes from the forward end surface 3a of the housing 2. However, in this modified embodiment, as shown in FIG. 4B, a plurality of, i.e., three switch members 35 are arranged at equal intervals (equal angles) around the center of the discharge port of the nozzle 16b. Note that the protruding heights of the respective switch members 35 are set to approximately identical heights. Further, three switch members 36, which correspond to the respective switch members 35, are arranged in the housing 2. Then, the three pairs of switch members 35, 36 are connected in series between the connecting terminal 30a and the plus terminal of the battery 30.

In the case of the syringe 1 according to this modified embodiment constructed as described above, all of the three switch members 35 slide into the housing, and the switch members 35 are brought in contact with the corresponding switch members 36 respectively. Accordingly, the conduction state is given between the connecting terminal 30a and the plus terminal of the battery 30, and the voltage application to the igniter 11 is performed. Accordingly, the slide of the three switch members 35 is required for the user as the preparatory operation for the syringe 1. Therefore, it is possible to consequently prompt the more careful preparatory operation. It is possible to precisely avoid any unintended discharge of the injection solution. Further, the three switch members 35 are arranged in the circumferential direction about the center of the discharge port of the nozzle 16b, and each of the plurality of switch members is arranged so that the distance from the nozzle 16b is identical. Therefore, when the three switch members 35 are simultaneously brought in contact with the injection target area and allowed to slide into the interior of the housing 2, then the attitudes or postures thereof are automatically controlled so that the syringe 1 is generally orthogonal to the injection target area. Accordingly, the attitude or posture of the syringe 1, which is suitable for the discharge of the injection solution, is secured.

Second Modified Embodiment

Figure 5A:
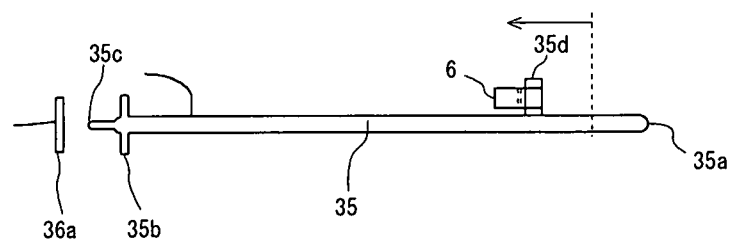
FIG. 5A schematically shows a second embodiment of the needleless syringe according to the present disclosure.

An explanation will now be made on the basis of FIGS. 5A-5C about a second modified embodiment of the syringe 1. The embodiment described above is constructed such that the spring portion 36b is arranged between the brim portion 35b of the switch member 35 and the brim portion 36a of the switch member 36, and the protruding state of the switch member 35 is maintained by the urging force exerted on the switch member 35. On the other hand, this modified embodiment adopts a structure to retain the protruding state in place of the spring portion 36b. Specifically, the protruding state is maintained by a maintaining member 6 which is fixed in the housing 2 and a columnar projecting portion 35d which is provided at a portion positioned at the inside of the housing 2 in a state in which the switch member 35 is not brought in contact with the injection target area (portion of the switch member 35 belonging to an area disposed on the left side with respect to a dotted line shown in FIG. 5A).

Figure 5B:
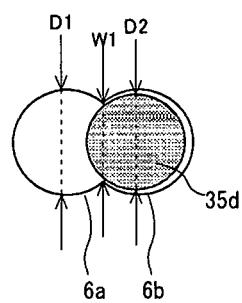
FIG. 5B schematically shows a second embodiment of the needleless syringe according to the present disclosure.
Figure 5C:
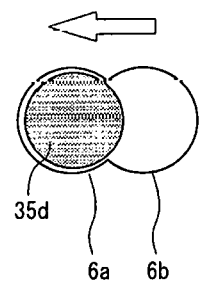
FIG. 5C schematically shows a second embodiment of the needleless syringe according to the present disclosure.

As shown in FIG. 5B, the maintaining member 6 has two through-holes 6a, 6b. The through-holes 6a, 6b are arranged so that parts of the circular through-holes are overlapped with each other to form a through-hole having a so-called daruma (tumbling doll)-shaped form (Venn diagram-like shape composed of two overlapping circles). Both of the through-holes 6a, 6b have the maximum width of D1. Then, the width W1, which forms the boundary between the through-holes 6a, 6b, is shorter than the width D1. In this arrangement, the diameter of the projecting portion 35d is D2 which is slightly smaller than the width D1 and which is slightly larger than the width W1. Then, in a state in which the forward end portion 35a of the switch member 35 protrudes, the projecting portion 35d is fitted into the through-hole 6b as shown in FIG. 5B. The diameter D2 of the projecting portion 35d is larger than the width W1. Therefore, if the pressing force, which acts on the forward end portion 35a in accordance with the contact with the injection target area, is not more than a predetermined value, the projecting portion 35d stays in the through-hole 6b.

On the other hand, if the pressing force is increased and the pressing force exceeds the predetermined value, then the maintaining member 6 is elastically deformed in the vicinity of the boundary between the through-holes 6a, 6b, and the width W1 of the boundary is widened. Accordingly, as shown in FIG. 5C, the projecting portion 35d moves from the through-hole 6b to the through-hole 6a. As a result, such a state is given that the switch member 35 is intruded into the housing 2 together with the forward end portion 35a, and the proximal end portion 35c is brought in contact with the brim portion 36a. Thus, the voltage application to the igniter 11 is executed. It is also possible to preferably avoid any unintended discharge of the injection solution by means of the syringe 1 which adopts the structure to maintain the switch member 35 as described above. Note that when the projecting portion 35 completely moves to the through-hole 6a, then the maintaining member 6 is restored from the elastic deformation in the vicinity of the boundary between the through-holes 6a, 6b, and the movement of the projecting portion 35d is restricted again. Note that in the exemplary arrangement shown in FIGS. 5A-5C, the projecting portion 35d may be elastically deformed as well. Further, other than the elastic deformation described above, the movement of the switch member 35 as described above may be realized by utilizing the plastic deformation of the maintaining member 6 and/or the projecting portion 35d.

Third Modified Embodiment

Figure 6:
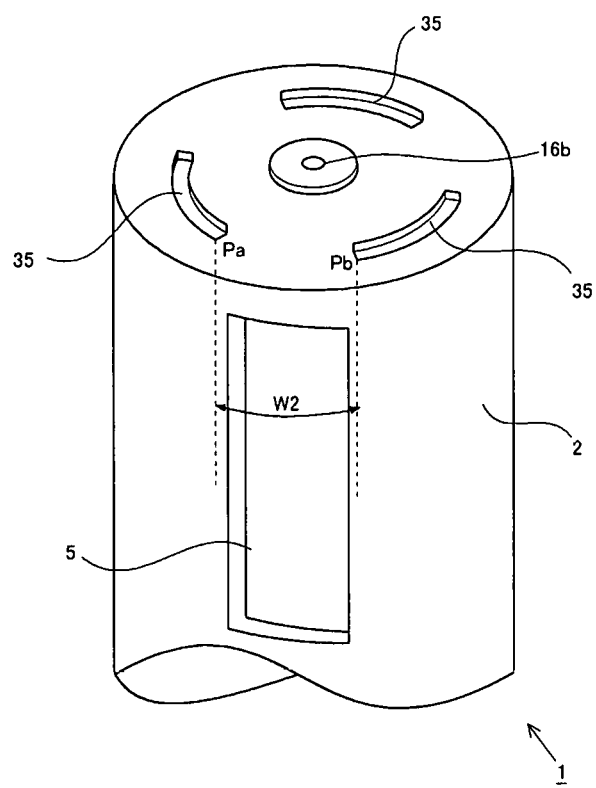
FIG. 6 schematically shows a third embodiment of the needleless syringe according to the present disclosure.

An explanation will now be made on the basis of FIG. 6 about a third modified embodiment of the syringe 1. FIG. 6 schematically shows the forward end side of the syringe. In the case of the syringe 1 shown in FIG. 6, forward end portions of three switch members 35 protrude to surround the discharge port of the nozzle 16b. Each of the switch members 35 is formed to have a band-shaped form having a predetermined width. The forward end portions of the switch members 35 form a discontinuous annular protruding portion as a whole. When the plurality of switch members 35 are arranged as described above, it is possible to preferably suppress any unintended discharge of the injection solution as described above. Further, it is possible to prevent the injection solution discharged upon the injection from being scattered to the surroundings to no small extent by means of the protruding portion formed to have the discontinuous annular shape.

Further, a visual recognition window 5 is arranged on the side surface of the housing 2 of the syringe 1 shown in FIG. 6 so that the state of the injection solution in the syringe unit 10 charged to the inside (for example, the presence or absence of the injection solution) can be visually recognized from the outside. The width of the visual recognition window 5 is set to be smaller than the distance W2 between the end portion Pa of one switch member 35 and the end portion Pb of the adjoining switch member 35. Accordingly, it is possible to avoid such a situation that the slide of the switch members 35 into the housing 2 interferes with the visual recognition window 5. Note that when one visual recognition window 5 is provided, then the switch members 35 may be separated from each other as shown in FIG. 6 at the portion corresponding to the window, and the switch members 35 may be connected to one another at the other portion to form a horseshoe-shaped switch member as a whole.

Figure 7:
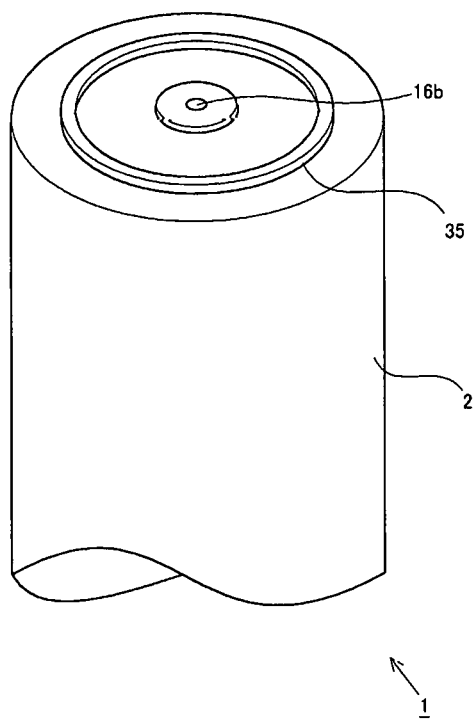
FIG. 7 schematically shows a fourth embodiment of the needleless syringe according to the present disclosure.

Further, when it is unnecessary to provide the visual recognition window 5, or when the visual recognition window 5 does not interfere with the slide of the switch member 35, then the switch member may be formed to have an annular shape to surround the discharge port of the nozzle 16b as shown in FIG. 7. When the structure as described above is adopted, it is possible to more reliably suppress the scattering of the discharged injection solution to the surroundings.

Second Embodiment

Figure 8:
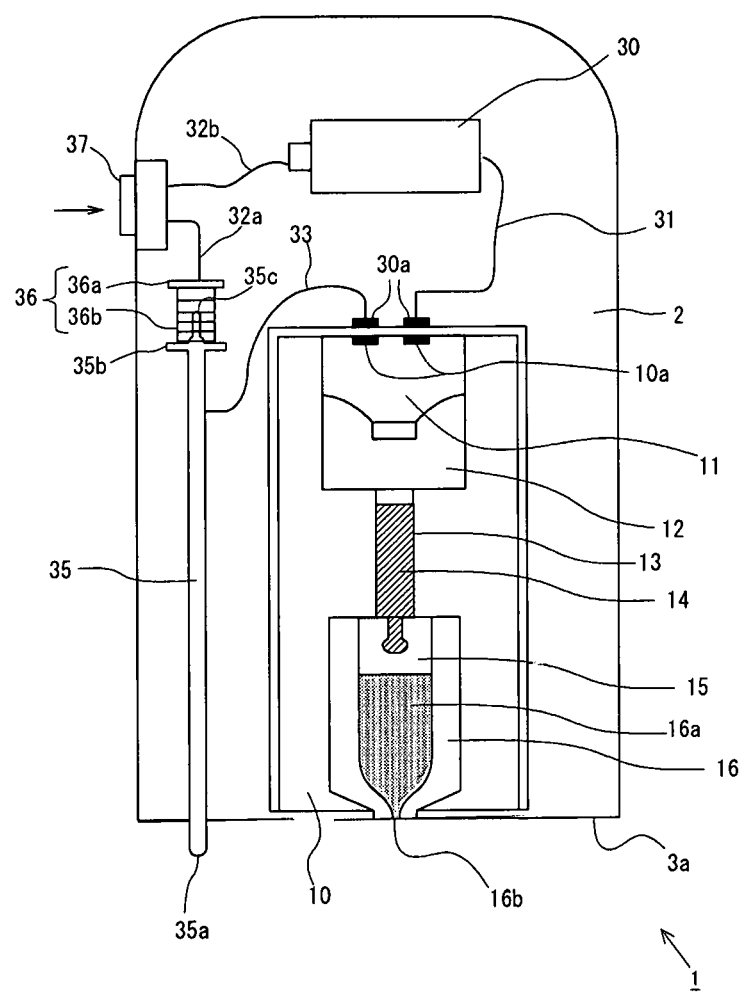
FIG. 8 schematically shows a fifth embodiment of the needleless syringe according to the present disclosure.

Next, an explanation will be made on the basis of FIG. 8 about a syringe 1 according to a second embodiment of the present disclosure. Note that the constitutive components or parts of the syringe 1 according to this embodiment, which are the same as the constitutive components or parts of the syringe according to the first embodiment described above, are designated by the same reference numerals, any detailed explanation of which will be omitted. The structure of the syringe 1 according to this embodiment is different from the structure of the syringe 1 shown in FIG. 2 in that an ignition switch 37, which is usable to control the voltage application from the battery 30 to the igniter 11, is further provided between the plus terminal of the battery 30 and the brim portion 36a of the switch member 36.

The ignition switch 37 is connected to the brim portion 36a via a wiring 32a, and the ignition switch 37 is connected to the plus terminal of the battery 30 via a wiring 32b. Then, the conduction state is given between the brim portion 36a and the plus terminal of the battery 30 in accordance with the pressing operation performed by a user for depressing a button included in the ignition switch 37. The direction of the pressing operation of the ignition switch 37 is orthogonal to the side surface of the housing 2. Therefore, the pressing operation direction is different by about 90 degrees from the slide direction of the switch member 35 along with the longitudinal direction of the housing 2.

In the case of the syringe 1 construct as described above, the user brings the discharge port of the nozzle 16b in contact with the injection target area to allow the switch members 35, 36 to be in the conduction state. Further, the user performs the pressing operation for the ignition switch 37. Thus, the voltage is applied to the igniter 11 and the injection solution can be discharged. In this way, another operation is required in addition to the operation for making the contact between the discharge port and the injection target area until arrival at the voltage application to the igniter 11. Thus, it is possible to more precisely avoid any unintended discharge of the injection solution. Further, as described above, the pressing operation direction of the ignition switch 37 is different from the slide direction of the switch member 35. Therefore, the clearly different operations are required for the user. Therefore, it is necessary that the respective operations should be performed independently. Therefore, this necessity contributes to the prevention of any unintended discharge of the injection solution.

Note that any one of the operation to provide the conduction state of the switch members 35, 36 and the pressing operation of the ignition switch 37 may be performed antecedently. Further, it is not necessarily indispensable that the ignition switch 37 forms the conduction state in accordance with the pressing operation. The ignition switch 37 may be a switch of such a type that the conduction state is formed by performing the slide operation for a slide switch. Also in this case, it is preferable that the slide direction of the slide switch is different from the slide direction of the switch member 35. Alternatively, the ignition switch 37 can be also constructed such that the ignition switch 37 cannot be operated, or the electric conduction is not caused even when the operation is performed, before the switch member 35 is moved from the first position to the second position.

Third Embodiment

Next, an explanation will be made on the basis of FIG. 9 about a syringe 1 according to a third embodiment of the present disclosure. Note that the constitutive components or parts of the syringe 1 according to this embodiment, which are the same as the constitutive components or parts of the syringe according to the first embodiment described above, are designated by the same reference numerals, any detailed explanation of which will be omitted. The structure of the syringe 1 according to this embodiment is different from the structure of the syringe 1 shown in FIG. 2 in that a syringe unit 10 itself protrudes from the surface 3b of the forward end surface 3 of the housing 2 in place of the switch member 35. Therefore, the syringe 1 shown in FIG. 9 does not adopt the structure of the switch members 35, 36 described above.

Figure 9:
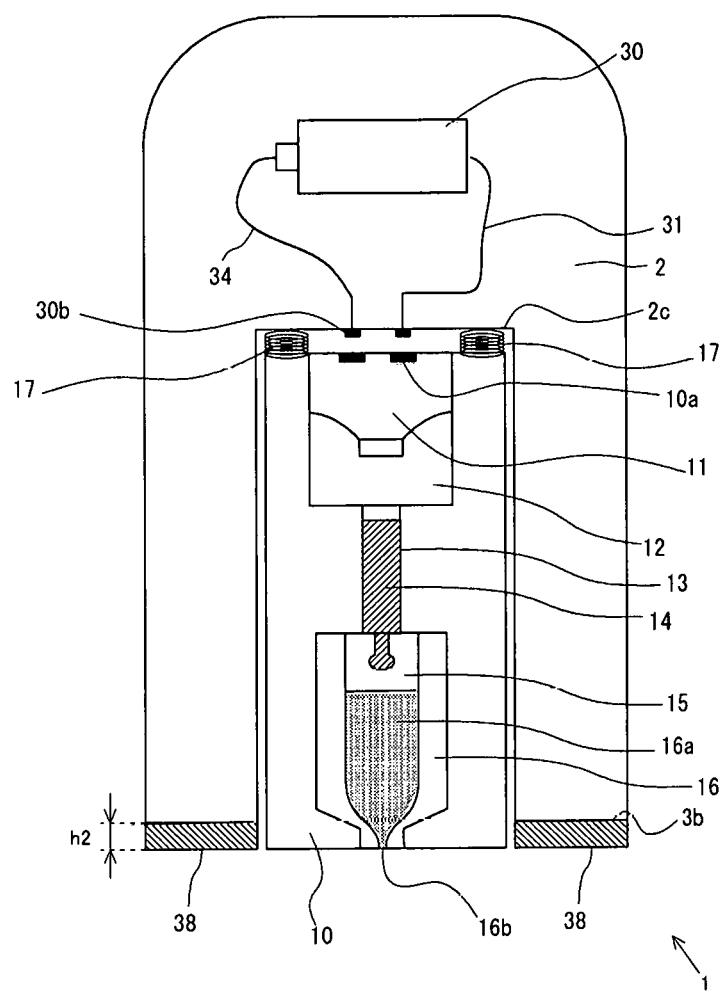
FIG. 9 schematically shows a sixth embodiment of the needleless syringe according to the present disclosure.

In the case of the syringe 1 shown in FIG. 9, the syringe unit 10 is charged into the housing 2 so that the discharge port of the nozzle 16b included in the syringe unit 10 protrudes by a height h2 from the surface 3b of the forward end surface 3 of the housing 2. Then, the syringe unit 10 is connected to the housing 2 by the aid of a spring portion 17 so that the syringe unit 10 is slidable in the longitudinal direction in the housing 2. Further, connecting terminals 30b, which are connected to the plus terminal and the minus terminal of the battery 30, are formed in projection-shaped forms on the bottom surface 2c of the housing 2. When the syringe unit 10 slides toward the bottom surface 2c, then the contact is made with the connecting terminal 10a disposed on the side of the syringe unit 10, and thus the output voltage of the battery 30 is applied to the igniter 11.

When the external force does not act on the syringe unit 10, a state is given, in which the position of the discharge port of the nozzle 16b protrudes from the forward end surface 3b by the height h2 in accordance with the balance with respect to the urging force of the spring portion 17. In this situation, the connecting terminal 30b and the connecting terminal 10a are not brought in contact with each other, and hence the voltage is not applied to the igniter 11. In the case of the syringe 1 constructed as described above, the user brings the discharge port of the nozzle 16b in contact with the surface of the injection target area, and the user intrudes the syringe unit 10 into the housing while retaining the contact state. Accordingly, the connecting terminal 30b and the connecting terminal 10a can be brought in contact with each other, and the igniter 11 can be allowed to perform the voltage application and the discharge of the injection solution. Therefore, in order to apply the voltage to the igniter 11, it is necessary for the user to maintain such a state that the syringe unit 10 is intruded into the housing 2 in a state in which the discharge port of the nozzle 16b is brought in contact with the injection target area. Also in the case of the syringe 1 shown in FIG. 9, the preparatory operation and the discharge execution operation of the user are correlated with each other by the aid of the syringe unit 10 which corresponds to the protruding member according to the present disclosure. Thus, it is possible to avoid any unintended discharge of the injection solution in the case of the syringe 1 as well.

Note that when the syringe unit 10 protrudes from the forward end surface 3b of the housing 2, it may be also considered that there is such a fear that the forward end of the syringe unit 10 may be brought in contact with any one other than the injection target area, and the voltage may be carelessly applied to the igniter 11. In view of the above, as shown in FIG. 9, an elastic sheet 38, which has a thickness corresponding to the protruding height h2 of the syringe unit 10, is provided on the surface 3b of the forward end surface 3 of the housing 2 so that the surface of the elastic sheet 38 is flush with the forward end surface of the syringe unit 10 (position of the discharge port of the nozzle 16b). The elastic sheet 38 is formed to have a sheet-shaped form with an elastic member such as sponge, rubber or the like. In this way, the protruding state of the syringe unit 10 is hidden by the elastic sheet 38. Accordingly, it is possible to avoid such a situation that any external force carelessly acts on the syringe unit 10. In the case of the syringe 1 constructed as described above, when the user brings the discharge port of the nozzle 16b in contact with the surface of the injection target area, and the user intrudes the syringe unit 10 into the housing while retaining the contact state so as to compress the elastic sheet 38, then the connecting terminal 30b and the connecting terminal 10a can be thereby brought in contact with each other, and it is possible to perform the voltage application to the igniter 11 and perform the discharge of the injection solution. Note that the slide amount h2' of the syringe unit 10, which enables the voltage application to the igniter 11, may be set to a value smaller than h2 described above in consideration of the thickness of the elastic sheet 38. Further, in the embodiment shown in FIG. 9, the syringe unit 10 and the housing 2 may be assembled by utilizing the fitting relationship as shown in FIGS. 5A-5C in place of the spring portion 17. Further, the ignition switch 37 as shown in FIG. 8 may be used in combination.

OTHER EMBODIMENTS

According to the syringe 1 of the present disclosure, for example, cultured cells, stem cells, and the like may be seeded or inoculated into injection target cells or scaffold tissues (scaffolds) in the field of the regenerative medicine of human, in addition to the case where the injection solution is injected into the skin structure. For example, as described in Japanese Patent Application Publication No. 2008-206477, the syringe 1 may inject cells which may be appropriately determined by those skilled in the art depending on a transplantation portion and the purpose of the cell regeneration, for example, endothelial cells, endothelial precursor cells, myeloid cells, preosteoblast, chondrocytes, fibroblast, skin cells, muscle cells, liver cells, kidney cells, intestinal tract cells, and stem cells, as well as all cells considered in the field of the regenerative medicine.

Further, the syringe 1 of the present disclosure may be also used for delivering DNA or the like to cells or scaffold tissues (scaffolds) as described in Japanese Translation of PCT International Application Publication No. 2007-525192. In this case, it is possible to suppress an adverse effect on cells themselves or scaffold tissues (scaffolds) themselves when the syringe 1 of the present disclosure is used, as compared with when the delivery is performed using a needle. Therefore, it can be said that the use of the syringe 1 is more desirable.

Further, the syringe 1 of the present disclosure is ideally useful, for example, when various genes, cancer inhibiting cells, lipid envelops, and the like are directly delivered to target tissues and when antigen genes are administered to enhance the immunity against pathogens. In addition to the above, the syringe 1 can be also used, for example, in the field of medical treatment for various diseases (for example, see Japanese Translation of PCT International Application Publication Nos. 2008-508881 and 2010-503616) and the field of immunological medical treatment (for example, see Japanese Translation of PCT International Application Publication No. 2005-523679). The field, in which the syringe 1 is usable, is not intentionally limited.

What is claimed is:

1. A needleless syringe for injecting an injection objective substance into an injection target area by discharging the injection objective substance without using any injection needle, the needleless syringe comprising:
    an accommodating unit provided in a housing of the needleless syringe and configured to accommodate the injection objective substance;
    a driving unit configured to operate when a voltage is applied to generate discharge energy in order to discharge the injection objective substance accommodated in the accommodating unit;
    a nozzle unit including a flow passage for allowing the injection objective substance applied with the discharge energy generated by the driving unit to flow therethrough and configured to discharge the injection objective substance from a discharge port formed at a forward end of the flow passage;
    a protruding member which is provided movably from a first position, at which a forward end of the protruding member protrudes from an end surface of the housing, to a second position at which 1) a protruding length of the forward end of the protruding member from the end surface of the housing is shorter than a protruding length of the forward end of the protruding member at the first position and 2) the forward end of the protruding member and the discharge port can be brought in contact with the injection target area, at least a portion of the protruding member configured to slide from an exterior of the housing into an interior of the housing via an opening formed in the end surface of the housing when the protruding member moves from the first position to the second position, the end surface of the housing configured to directly contact the injection target area;
    a maintaining mechanism configured to maintain the protruding member at the first position before the discharge energy is generated by the driving unit; and
    a power source circuit configured to apply a voltage to the driving unit when the protruding member having been maintained at the first position is moved to the second position by means of a pressing force received by the forward end of the protruding member.

2. The needleless syringe according to claim 1, wherein the first position is a position at which the forward end of the protruding member protrudes from the discharge port.

3. The needleless syringe according to claim 1, wherein the protruding member is formed by an annular member which surrounds the discharge port.

4. The needleless syringe according to claim 1, wherein:
    the protruding member is provided in plural; and
    the power source circuit is configured to apply the voltage to the driving unit in accordance with movement of all of the plurality of protruding members to the second position.

5. The needleless syringe according to claim 4, wherein the plurality of protruding members are arranged in a circumferential direction around the discharge port on the end surface of the housing.

6. The needleless syringe according to claim 4, wherein:
    the housing has a visual recognition window which is provided on a side surface thereof in order to visually recognize the interior of the housing;
    the accommodating unit is formed so that the accommodated injection objective substance can be visually recognized from the exterior of the housing through the visual recognition window; and
    the plurality of protruding members are arranged respectively not to overlap the visual recognition window before and after the movement from the first position to the second position.

7. The needleless syringe according to claim 1, further comprising:
    a syringe unit which collectively stores, as one unit, the accommodating unit, the driving unit, and the nozzle unit in the housing, so that the discharge port of the nozzle unit is arranged at a forward end of the unit, wherein:
    the protruding member is formed as the syringe unit, and the first position is a position at which the forward end of the syringe unit protrudes from the end surface of the housing.

8. The needleless syringe according to claim 7, further comprising:
    an annular elastic cover which is arranged on the end surface of the housing and which surrounds the forward end of the syringe unit, wherein:
    the cover is formed so that a protruding length of the forward end of the cover from the end surface of the housing is not less than a protruding length of the forward end of the syringe unit from the end surface of the housing when the syringe unit is disposed at the first position, and the cover allows the syringe unit to move to the second position by being elastically deformed by the pressing force when the pressing force is applied to the syringe unit.

9. The needleless syringe according to claim 1, further comprising:

an operation switch configured to operate in accordance with an operation of a user in relation to the voltage application from the power source circuit to the driving unit in a direction different from a direction of the movement of the protruding member from the first position to the second position, wherein:

the power source circuit is configured to apply the voltage to the driving unit when the protruding member arrives at the second position and the operation switch is operated so that the voltage can be applied.

10. The needleless syringe according to claim 1, wherein the maintaining mechanism has an urging member configured to urge the protruding member in a protruding direction thereof by means of a predetermined urging force.

11. The needleless syringe according to claim 1, wherein the maintaining mechanism is formed so that the maintaining mechanism maintains the protruding member at the first position against the pressing force if the pressing force is not more than a predetermined value, while the maintaining mechanism allows the protruding member to move to the second position if the pressing force is larger than the predetermined value.

12. The needleless syringe according to claim 1, wherein the at least portion of the protruding member is configured to slide out of the housing via the opening when the protruding member moves from the second position to the first position such that the at least portion of the protruding member is exposed outside of the housing.

13. The needleless syringe according to claim 1, wherein the forward end of the protruding member is configured to activate the power source circuit when the forward end of the protruding member directly contacts and is pressed against the injection target area.

14. The needleless syringe according to claim 13, wherein the portion of the protruding member is configured to slide into the interior of the housing via the opening when the forward end of the protruding member is pressed against the injection target area.

15. The needleless syringe according to claim 1, wherein a first portion of the protruding member is disposed inside the housing and a second portion of the protruding member is disposed outside the housing, in the first position.

16. The needleless syringe according to claim 15, wherein the first portion of the protruding member is longer than the second portion of the protruding member.

* * * * *